United States Patent [19]

Wilk

[11] Patent Number: 5,314,436
[45] Date of Patent: May 24, 1994

[54] METHOD AND APPARATUS FOR PERFORMING END-TO-END ANASTOMOSES

[76] Inventor: Peter J. Wilk, 185 West End Ave., New York, N.Y. 10023

[21] Appl. No.: 969,744
[22] Filed: Oct. 30, 1992
[51] Int. Cl.$^5$ .............................................. A61B 17/00
[52] U.S. Cl. .................................... 606/153; 606/151; 227/179; 227/180
[58] Field of Search ................ 606/153; 227/179, 180

[56] References Cited

U.S. PATENT DOCUMENTS

| | | | |
|---|---|---|---|
| 4,899,744 | 2/1990 | Fujitsuka et al. | 606/153 |
| 5,123,908 | 6/1992 | Chen | 606/153 |
| 5,188,638 | 2/1993 | Tzakis | 606/153 |

Primary Examiner—Stephen C. Pellegrino
Assistant Examiner—Gary Jackson
Attorney, Agent, or Firm—R. Neil Sudol; Henry D. Coleman

[57] ABSTRACT

A device for use in performing an end-to-end anastomosis comprises a stapling member insertable into a first end segment of a tubular organ, a plurality of staples arranged in a circular array in the stapling member, and an anvil member insertable into a second end segment of the tubular organ. The anvil member is movably connected to the stapling member to enable a clamping of the first and the second end segment to one another in juxtapositon to the circular array. A staple ejector is provided in the stapling member for ejecting the staples in a radial direction towards the anvil member, thereby stapling the first and the second end segment to one another along an annular locus.

5 Claims, 1 Drawing Sheet

METHOD AND APPARATUS FOR PERFORMING END-TO-END ANASTOMOSES

BACKGROUND OF THE INVENTION

This invention relates to a device or apparatus for use in performing end-to-end anastomoses. This invention also relates to an associated method for performing end-to-end anastomoses.

Where the colon is ressected, for example, owing to trauma or in corrective cancer surgery, the loose ends must be connected to one another to form a continuous, functioning colon. This connection or reconnection is commonly performed with a stapling instrument comprising a stapling member inserted through the rectum and into a first closed colon segment. An anvil member is inserted through the open end of another colon segment. That open end is then closed via a purse-string tie about a shaft projecting from the anvil member. The shaft is subsequently attached in telescoping fashion to a rod projection through the first colon segment from the stapling member.

Upon a connection of the stapling memebr and the anvil member, the two section are drawn towards one another via a screw mechanism operated from the proximal end of the stapling member, i.e., from outside the rectum. The closed ends of the colon segments are thus clamped between the stapling member and the anvil member of the anastomosis device. Upon completion of the clamping operation, the staples are ejected in two staggered circular arrays in a distal, axial direction from the stapling member towards the anvil member. Simultaneously, or immediately after the stapling operation, a circular blade is pushed in the distal direction from the stapling member axially towards the anvil member, thereby opening the colon segments to communication with one another.

After the stapling and cutting operation, the entire instrument is removed out through the rectum. Frequently, there is some difficulty in removing the instrument owing to the fact that the diameter of the colon segments at the anastomosis joint is smaller than the diameter of the instrument, particularly the anvil which must be pulled through the anastomosis joint.

OBJECTS OF THE INVENTION

An object of the present invention is to provide an improved anastomosis device or apparatus.

A related object of the present invention is to provide an improved method for performing an anastomosis operation.

Another, more particular, object of the present invention is to provide an anastomosis device or apparatus and an associated method which results in a larger anastomosis joint for the same diameter apparatus.

These and other objects of the present invention will be apparent from the drawings and detailed descriptions herein.

SUMMARY OF THE INVENTION

A device for use in performing an end-to-end anastomosis comprises, in accordance with the present invention, a stapling member insertable into a first end segment of a tubular organ, a plurality of staples arranged in a circular array in the stapling member, and an anvil member insertable into a second end segment of the tubular organ. The anvil member is movably connected to the stapling member to enable a clamping of the first and the second end segment to one another in juxtapositon to the circular array. A staple ejector is provided in the stapling member for ejecting the staples in a radial direction towards the anvil member, thereby stapling the first and the second end segment to one another along an annular locus.

Pursuant to another feature of the present invention, the anvil member is a female member and the stapling member is a male member, while the staples are ejected in a radially outward direction during operation of the staple ejector.

A cutter is provided on the stapling member for severing closed ends of the end segments, thereby opening the end segments to communication with one another.

A method for use in performing an end-to-end anastomosis comprises, in accordance with the present invention, the steps of (a) inserting a stapling member into a first end segment of a tubular organ, the stapling member having a plurality of staples arranged in a circular array, (b) inserting an anvil member into a second end segment of the tubular organ, (c) moving the anvil member and the stapling member towards one another so as to clamp the organ end segments between the stapling member and the anvil member in juxtapositon to the circular array, and (d) ejecting the staples in a radial direction from the stapling member towards the anvil member, thereby stapling the organ end segments to one another along an annular locus.

According to another feature of the present invention, the anvil member is a female member and the stapling member is a male member, the staples being ejected in a radially outward direction.

An improved anastomosis device or apparatus and an associated method in accordance with the present invention result in a larger anastomosis joint for the same diameter apparatus.

DETAILED DESCRIPTION

Figure 1:
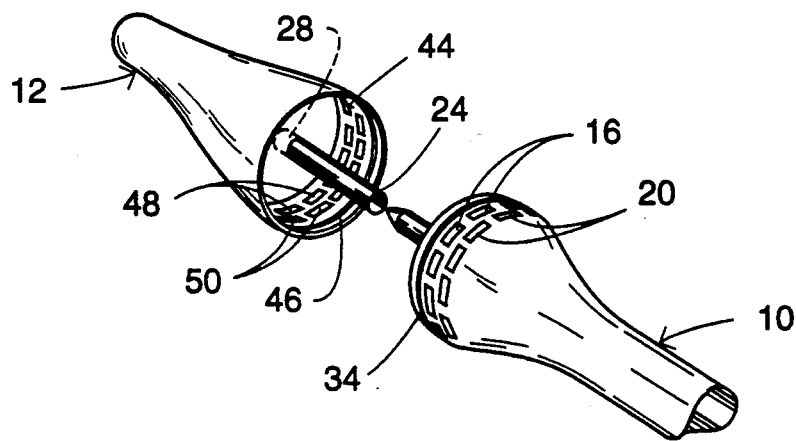
FIG. 1 is a partial schematic perspective view of an end-to-end or intraluminal anastomosis device in accordance with the present invention.

As illustrated in FIG. 1, a device for use in performing an end-to-end anastomosis comprises a stapling member 10 which is insertable into a first end segment FES (FIGS. 4 and 5) of a tubular organ TO and an anvil member 12 insertable into a second end segment SES (FIGS. 4 and 5) of tubular organ TO. Anvil member 12 is a female member, while stapling member 10 is a male member insertable into anvil member 12 together with end tissues of end segments FES and SES.

Figure 2:
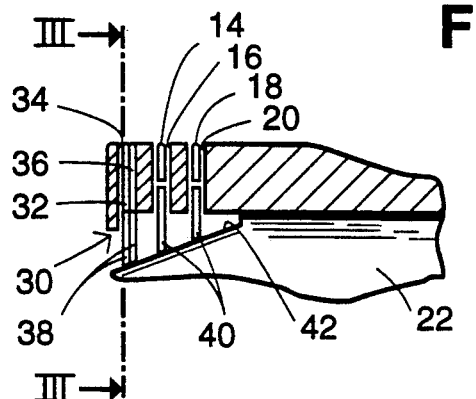
FIG. 2 is a partial longitudinal cross-sectional view of a stapling member of the device shown in FIG. 1.

As illustrated in FIGS. 1 and 2, a plurality of staples 14 are arranged in a first circular array in respective recesses 16 in stapling member 10. Proximally of staples 14 is another plurality of staples 18 disposed in a second circular array in respective recesses 20. Staples 14 and 18 and respective recesses 16 and 20 are oriented in radial planes so that, upon a distally directed stroke of an ejection member 22 (FIG. 2), staples 14 and 18 are ejected in a radially outward direction in the planes of their respective arrays to thereby staple end segments FES and SES to one another along an annular locus. Ejection member 22 is shifted distally by an actuating mechanism as found in conventional end-to-end anastomosis instruments.

Anvil member 12 is movably connected to stapling member 10 via female and male connector elements 24 and 26 during a stapling operation to enable a clamping of the organ end segments FES aand SES (FIGS. 4 and 5) to one another in the region of staples 14 and 18. Female connector element 24 (not shown in FIGS. 4 and 5) protrudes from the respective organ end segment SES and receives male connector element 26 to lock end segments FES and SES to one another.

As an alternative to protruding or projecting female connector element 24, anvil member 12 may be formed with a recess 28 for receiving male connector element 26 upon a piercing of second end segment SES thereby during a clamping operation. The use of this alternative is described hereinafter with reference to FIG. 5.

Figure 3:
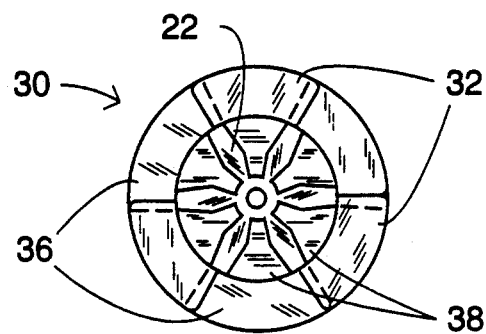
FIG. 3 is a transverse cross-sectional view taken along line III—III in FIG. 2.

As further illustrated in FIGS. 1-3, stapling member 10 is provided with a cutter assembly 30 for severing closed ends of organ end segments FES and SES, thereby opening the end segments to communication with one another upon completion of the stapling operation and prior to the termination of the anastomosis procedure. Cutting assembly 30 includes a first plurality of arcuate blades 32 circumferentially spaced from one another in a recess 34 in stapling member 110 and further includes a second plurality of arcuate blades 36 circumferentially spaced from one another in recess 34 and angularly staggered with respect to blades 32 so as to form a substantially continuous cutting edge. Blades 32 and 36 are pushed radially outwardly in response to the distally direction motion of ejection member 22 during a stapling operation. Between blades 32 and 36, on the one hand, and ejection member 22, on the other hand, are disposed camming elements 38 which eject blades 32 and 36 under the action of ejection memebr 22. Similarly, staples 14 and 18 are ejected by respective camming elements 40 which ride along a conical camming surface 42 of ejection member 22 and push staples 14 and 18 radially outwardly during a stapling operation.

Anvil member 12 is provided along an inner surface 44 with an annular groove 46 for receiving the outer, cutting edges of blades 32 and 36 during a stapling and cutting operation. Inner surface 44 is also formed with two arrays of short recesses 48 and 50 for receiving the legs of staples 14 and 18 and bending those legs to close the staples.

Figure 4:
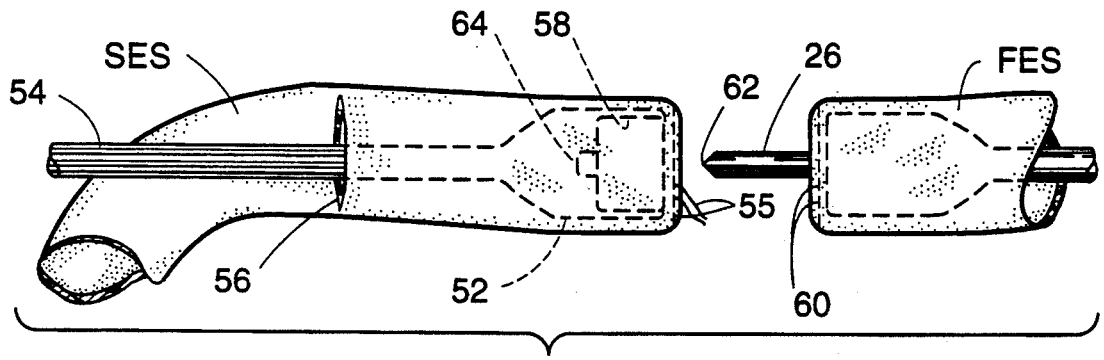
FIG. 4 is a schematic side elevational view showing a step in an end-to-end or intraluminal anastomosis procedure in accordance with the present invention.

In an anastomosis procedure illustrated in part in FIG. 4, an anvil member 52 is provided at the end of an elongate rod 54. End segment SES is closed by sutures or a purse type string 55 and anvil member 52 is inserted into the closed end segment via a colotomy or incision 56. As described hereinabove with reference to FIG. 1, anvil member 52 is a female member having a cylindrical recess 58 for receiving the closed ends of organ end segmetns FES and SES and stapling device 10. As in conventional anastomoses procedures, stapling device 10 is inserted through the rectum of the patient into end segment FES upon a closure of the free end thereof by sutures 60 or otherwise. Upon the insertion of stapling device into end segment FES, male connector element 26 is ejected in a distal direction through the closed end of end segment FES, as shown in FIG. 4.

Male connector element 26 has a sharp tip 62 and is pushed through the closed end of segment SES and inserted into a recess 64 in anvil member 52. Upon connection of the stapling member 10 and anvil member 52 via male connector element 26 and recess 64, connector element 26 is drawn back into stapling device 10, thereby clamping the closed ends of organ segments FES and SES to one another. Subsequently, ejection member 22 is shifted in the distal direction to eject staples 14 and 18 and blades 32 and 36 in a radially outward direction towards recesses such as recesses 48, 50 and 46 (FIGS. 1 and 2) in anvil member 52.

Upon completion of the stapling and cutting operations, ejection member 22 is shifted in the proximal direction, thereby allowing blades 32 and 36 to fall back into stapling device 10. Blades 32 and 36 may be spring loaded to facilitate the retraction of the blades back into stapling member 10. Anvil member is 52 is then pulled out of the connected end segments FES and SES via incision 56 and the incision is sutured closed. Stapling member 10 is withdrawn from end segments FES and SES via the rectum.

Figure 5:
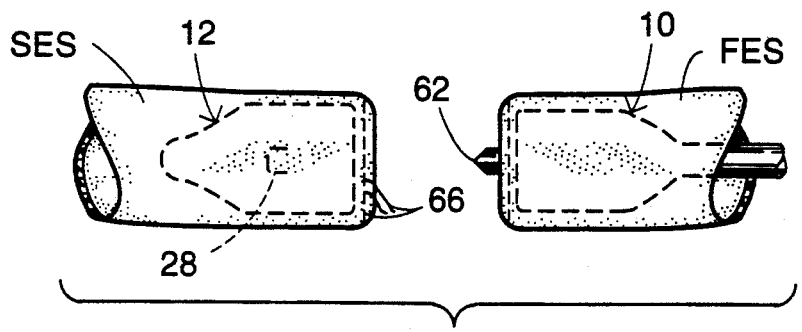
FIG. 5 is a schematic side elevational view showing a step in another end-to-end or intraluminal anastomosis procedure in accordance with the present invention.

In the procedure partially illustrated in FIG. 5, anvil member 12 is inserted into end segment SES via an open free end thereof. The opening is then closed via a purse type string suture 66. Stapling device 10 is inserted into end segment FES via the patient's rectum. The stapling operation then procedures as described hereinabove with reference to FIG. 4. Upon termination of the staping and cutting operations, and the retraction of the cutting blades 32 and 36, stapling member 10 is pushed further in the distal direction to disengage the clamped tissues or the connected organ segments FES and SES. Subsequently, the connected stapling and anvil members 10 and 12 are removed through the rectum.

It is to be noted that the anastomosis device described herein may be provided with radially movable clamping members (not shown) also actuated via a camming mechanism to firmly clamp the end segments FES and SES between stapling member 10 and anvil member 12. These clamping members may be radially shifted via a camming mechanism different from ejection member 22.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that in a modified embodiment of the anastomosis device, the female or anvil member may be inserted through the rectum into the first organ end segment FES. In that embodiment, the stapling device is inserted via a colotomoy or through the open end of the other organ end segment SES. To fire the staples and the cutting blades, an ejection member with a camming surface is shifted in a distal direction from the anvil member into the stapling member upon a connection of those two members and upon a clamping of the organs tissues between the two members.

Accordingly, it is to be understood that the drawings and descriptions herein are profferred by way of example to facilitate comprehension of the invention and should not be construed to limit the scope thereof.

What is claimed is:

1. A device for use in performing an end-to-end anastomosis, comprising:
   a stapling member insertable into a first end segment of a tubular organ;
   a plurality of staples arranged in a circular array in said stapling member;
   an anvil member insertable into a second end segment of said tubular organ, said stapling member being movably connected to and at least partially insertable into said anvil member to enable a clamping of said first and said second end segment to one another in juxtaposition to said circular array and between said stapling member and said anvil member; and
   staple ejection means in said stapling member for ejecting said staples in a substantially radial outward direction towards said anvil member and through said first and said second end segment, thereby stapling said first and said second end segment to one another along an annular locus.

2. The device defined in claim 1, further comprising cutting means on said stapling member for severing closed ends of said first and said second end segment, thereby opening said first and said second end segment to communication with one another.

3. A method for use in performing an end-to-end anastomosis, comprising the steps of:
   inserting a stapling member into a first end segment of a tubular organ, said stapling member having a plurality of staples arranged in a circular array;
   inserting an anvil member into a second end segment of said tubular organ;
   moving said anvil member and said stapling member towards one another so as to insert said stapling member at least partially into said anvil member and thereby clamp said first and said second end segment between said stapling member and said anvil member in juxtaposition to said circular array; and
   ejecting said staples in a substantially radial outward direction from said stapling member towards said anvil member and through said first end segment and said second end segment, thereby stapling said first and said second end segment to one another along an annular locus.

4. The method defined in claim 3 wherein said anvil member is a female member and said stapling member is a male member, said staples being ejected in a radially outward direction during operation of said staple ejection means.

5. A stapling member for cooperating performing with an anvil member to perform an end-to-end anastomosis, comprising:
   a body insertable into a first end segment of a tubular organ;
   a plurality of staple arranged in a circular array in said body, said staple having legs oriented in at least one substantially radial plane in said body;
   means on said body for movably connecting said body to the anvil member so that said body is inserted into said anvil member to enable a clamping of first and second end organ segments to one another in juxtaposition to said circular array of staples and between said body and said anvil member; and
   staple ejection means in said body for ejecting said staples in said plane towards said anvil member, thereby stapling said first and said second end segment to one another along an annular locus.

* * * * *

UNITED STATES PATENT AND TRADEMARK OFFICE
CERTIFICATE OF CORRECTION

PATENT NO. : 5,314,436
DATED : May 24, 1994
INVENTOR(S) : Peter J. Wilk

It is certified that error appears in the above-indentified patent and that said Letters Patent is hereby corrected as shown below:

Column 1, line 24, change "section" to --sections--.

Column 2, line 2, change "ton" to --tion--.

Column 3, line 33, change "110" to --10--; line 64, change "segmetns" to --segments--.

Column 4, line 1, insert --10-- after "device"; line 21, delete "is" (first occurrence); line 31, change "procedures" to --proceeds--; line 33, change "ing" to --ling--; line 57, change "colotomoy" to --colotomy--; line 62, change "organs" to --organ--.

Signed and Sealed this

Seventh Day of February, 1995

Attest:

BRUCE LEHMAN

Attesting Officer

Commissioner of Patents and Trademarks